United States Patent [19]

Feldschuh et al.

[11] Patent Number: 5,024,231
[45] Date of Patent: Jun. 18, 1991

[54] AUTOMATED MULTI-POINT BLOOD VOLUME ANALYZER

[75] Inventors: Joseph Feldschuh, New York; Jonathan A. Feldschuh, Barrytown, both of N.Y.

[73] Assignee: Daxor Corporation, New York, N.Y.

[21] Appl. No.: 522,741

[22] Filed: May 14, 1990

Related U.S. Application Data

[63] Continuation of Ser. No. 203,715, Jun. 7, 1988, abandoned.

[51] Int. Cl.$^5$ .................................................. A61B 6/00
[52] U.S. Cl. .................................... 128/654; 128/659; 128/713
[58] Field of Search ............... 128/637, 638, 654, 659, 128/713; 364/413.07

[56] References Cited

U.S. PATENT DOCUMENTS

3,727,048 4/1973 Haas .
4,055,083 10/1977 Haas .
4,120,295 10/1978 Hill .
4,197,836 4/1980 Wagner et al. .
4,313,928 2/1982 Kato et al. .......................... 128/659

OTHER PUBLICATIONS

Excerpt, Daxor Corporation 10K (1986), pp. 1 and 5-6.
The Wall Street Journal, Jan. 16, 1986, p. 13, and New York Newsday, Jan. 15, 1987.
Daxor Corporation, Annual Report (1985), p. 6.
Daxor Corporation, Annual Report (1986), pp. 1-2.
The Newsletter of Innovation—Breakthrough—by Boardroom Reports, vol. IV, No. 22 (Nov. 15, 1986).
"Problems of Probability Theory, Mathematical Statistics and Theory of Random Functions," edited by A. A. Sveshnikov, pp. 325-329.
Feldschuh et al, Circulation, vol. 56, No. 4, Oct. 1977, pp. 605-612.
Mollisan, Brit. J. of Haematology, vol. 25, 1973, pp. 801-814.
Tishchenko et al., Meditsinskaya Tekhnika, No. 1, Jan. Feb. 1980, pp. 39-42.

Primary Examiner—Lee S. Cohen
Attorney, Agent, or Firm—Amster, Rothstein & Ebenstein

[57] ABSTRACT

A multi-point method of determining a time-zero blood volume by the tracer dilution technique. A tracer is injected into the blood stream of a living being, and a plurality of mixed samples of blood and tracer are removed from the blood stream at a corresponding plurality of measured time intervals subsequent to the injecting step. A blood portion volume corresponding to each time interval is automatically determined from the tracer level in the mixed samples, and a time-zero blood portion volume is automatically calculated from the determined blood portion volumes and time intervals.

12 Claims, 2 Drawing Sheets

AUTOMATED MULTI-POINT BLOOD VOLUME ANALYZER

This is a continuation of co-pending application Ser. No. 203,715 filed on June 7, 1988, now abandoned.

BACKGROUND OF THE INVENTION

The present invention relates to methods of determining blood volume, and more particularly a method of determining blood volume by the indicator dilution technique.

Blood volume measurement data is usable by physicians in a variety of medical fields, including critical care, cardiology, pediatrics and surgery, to identify and quantify the amount of blood loss the patient has suffered, to determine the percentage of red blood cells or hemoglobin the patient has lost, and to help to determine the need for continuing treatment. An estimated twelve million blood transfusions per year are performed in U.S. hospitals. If rapid and economic blood volume measurement equipment were available in a hospital, it would be feasible to routinely perform a blood volume test on every patient for whom a blood transfusion appeared to be indicated. Blood volume measurement would also provide a valuable diagnostic tool in treating certain types of heart and kidney disease.

The ability to accurately measure the quantity or volume of blood in an individual would be expected to be particularly useful in surgical situations. The standard methods of estimating the amount of blood an individual has are called the hematocrit or hemoglobin. These tests actually measure the thickness of an individual's blood. Blood is composed of cells, primarily red cells for carrying oxygen, white cells for fighting infections, and platelets, small cells used for clotting purposes. The remainder of the blood is called the plasma, which is primarily water in which are suspended the cells with various clotting factors and special blood proteins. When an individual bleeds, the body will attempt to maintain the same total blood volume by the transfer of water from other parts of the body into the circulatory system. This process causes a thinning of the blood called anemia. The thinning process may take hours or many days to occur or may never occur completely. When the blood thinning process has not occurred completely, the hematocrit will over-estimate the amount of blood the individual actually has.

The more rapid the blood loss, the less likely the hematocrit will reflect the true picture of the patient's blood volume. For example, an individual who has just donated a pint of blood (usually over a 10–15 minute period) obviously has one pint less blood at the end of the donation than at the beginning. Yet a hematocrit measurement at the beginning and at the end of the donation may be almost unchanged, therefore giving no indication that the individual has just lost a pint of blood. Surgery is a situation in which individuals lose relatively large quantities of blood in a short time. Despite infusion of saline and other blood diluters, the hematocrit is frequently very misleading at the end of surgery as to the quantity of blood lost. Patients may have lost 25 to 35 percent more blood than estimated from hematocrit measurement and the weighing of blood-soaked sponges. Patients losing more than 2 pints may have circulatory collapse when undergoing anesthesia.

At the present time, human blood volume is generally measured by indirect means. Blood volume is estimated indirectly by tests which essentially measure the ratio of red blood cells to the plasma (the fluid in which the blood cells are suspended) in a blood sample. Blood volume is inferred from measurement of the hematocrit (the percentage of the blood which is made up of red blood cells). This indirect measure of blood volume actually measures the degree of plasma dilution of the blood. When the hematocrit of a patient's blood drops, the patient is said to be anemic. When that hematocrit is very low, the physician assumes that the dilution is the result of a loss in blood volume and that the patient may require a blood transfusion.

The current approach to human blood volume measurement has several serious drawbacks. When an individual bleeds after surgery or trauma, the body's immediate response is to constrict blood vessels to maintain circulation with a lesser liquid volume. It may take hours or days for the body's production of plasma, which replaces the fluid loss, to cause the remaining blood cells to become diluted so that the degree of blood loss will be accurately reflected by the hematocrit. In addition, diseases such as cancer or kidney disease may damage the plasma protein system so that the patient is unable to produce sufficient plasma to dilute the remaining red blood cells. If this occurs, the patient's blood deficiency may be seriously underestimated and inadequate or incorrect treatment given. Conversely, disease such as polycythemia (a condition marked by an abnormally large number of red blood cells in the blood) can increase the number of red blood cells although plasma volume remains the same or decreases. The presence of this type of disease may mask a drop in the patient's blood volume which requires transfusion therapy.

Direct measurement of human blood volume can be much more accurate than the indirect methods which are currently used. Direct measurement is currently accomplished by the indicator dilution technique involving the injection into the blood stream of an indicator or tracer, such as a radioactive isotope or chemical dye, attached to either the plasma protein portion of the plasma or the red cell portion of the blood. The degree of dilution of the tracer is inversely related to the volume of the patient's blood. Direct measurement of a patient's plasma volume is usually accomplished by injection directly into the patient of an isotope (such as $I^{125}$ or $I^{131}$) or a chemical dye, such as Evan's Blue Dye, attached to a plasma protein of a type normally suspended in the plasma. Through chemical analysis or use of a gamma counter, the degree of dilution of the tracer is then ascertained and mathematically related to the absolute measurement of the patient's blood volume.

While these direct measurement techniques can produce a much more accurate measurement of blood volume, they have been subject to multiple problems. Physically, it is impossible to achieve instantaneous total mixing of the tracer with the patient's blood plasma. As the tracer mixes, the dye or radioactive isotope leaves the circulatory system at a variable rate. In addition, the use of tiny amounts of tracer requires extreme precision in the injection and sampling process, with relatively small errors resulting in greatly magnified errors in the final measurement. These errors can occur without detection and can be caused by common factors such as the anti-coagulants which are necessary to obtain a sample. Also, blood samples obtained from a normal peripheral vein do not give a true reading of the mean body hematocrit. Some physicians are unaware of these potential inaccuracies and may erroneously estimate the amount of blood needed for transfusion. A common problem after surgery is estimating the amount of blood loss and the amount of transfusions required to correct blood loss. Notwithstanding the problems, it has been possible using meticulous techniques involving multiple samples and the measurement and calculation of 28 to 36 variables to accurately measure an individual's blood volume at a given instant.

Before measurement of blood volume is useful for purposes of diagnosis and treatment, however, it is necessary for a physician or diagnostician to know the "normal" range of blood volumes for a given individual. Without knowing what is normal for a specific person, the physician cannot determine the degree to which his blood volume readings, even performed with great accuracy, indicate loss of blood or a disease state. Many studies have been conducted to determine what constitutes a normal blood volume range for a specific individual. These studies have used multiple techniques, the most common have been body weight or surface area blood volume ratios. In 1977, an alternative method was developed which provides an explanation for systematic errors which had been noted in previous studies. Using these methods, the alternative method provides a new theoretical framework for these calculations which eliminate these systematic errors. These calculation methods, however, are time-consuming and difficult to perform. This problem, coupled with the previously described difficulty of performing accurate blood volume measurement by direct means, has restricted use of direct measurement of blood volume to research situations.

The many hours required to perform the meticulous techniques, involving multiple samplings and the measurement and calculation of 28 to 36 variables, insure that the resultant accurate measurement is available far too late to provide guidance for the critical decisions which must typically be made instantly or at least in some semblance of real time in order to be of value to a living patient. For the purpose of the present invention, real time decisions are defined as those which can be made within 20 minutes of the taking of the last sample from the patient.

Accordingly, it is an object of the present invention to provide a method for obtaining by direct measurement techniques a measurement of blood volume in real time.

Another object is to provide such a method which determines a true time-zero blood volume from a multipoint calculation.

A further object is to provide such a method which optionally compares the calculated blood volumes to a normal volume for the patient.

It is also an object of the present invention to provide apparatus for carrying out such a method in real time.

SUMMARY OF THE INVENTION

It has now been found that the above and related objects of the present invention are attained in a multipoint method of determining a time-zero blood volume by the indicator dilution technique. The method comprises the steps of injecting an indicator into the blood stream of a living being and removing a plurality of mixed samples of blood and indicator from the blood stream at a corresponding plurality of measured (optionally irregular) time intervals subsequent to the injecting step. From the level of indicator in the mixed samples, a blood-portion volume corresponding to each time interval is automatically determined. Finally, a time-zero blood portion volume is automatically calculated from the determined blood portion volumes and time intervals, preferably by logarithmic regression analysis.

For enhanced accuracy, the blood portion volume/time interval data is analyzed for general agreement, and any such data not in general agreement with the remainder of such data is disregarded in the determination of the time-zero blood portion volume.

In a preferred embodiment, the indicator is a radioactive tracer (e.g. $I^{131}$-tagged albumin), and the determination of the indicator level employs a gamma counter (e.g., an NaI scintillation gamma counter).

The hematocrit of each mixed sample is also determined, and the whole blood volume and red cell mass are calculated for each mixed sample using the hematocrit therefor. The indicator level of a fixed plasma amount from the mixed sample is automatically determined, and the plasma volume of the mixed sample corresponding to a known time interval is automatically determined by reference to known standards.

The present invention further comprises an automated multi-point time-zero blood volume analyzer. The analyzer comprises means for receiving a plurality of mixed samples of blood and an indicator injected into a blood stream from which the sample is taken, the indicator having been injected at a given time and the samples being taken at measured time intervals thereafter. The analyzer further comprises means for automatically determining from the indicator levels in the mixed samples a blood portion volume corresponding to each time interval, and means for automatically calculating a time-zero blood portion volume from the determined blood portion volumes and time intervals.

In a preferred embodiment the analyzer further comprises means for receiving environment background samples, standard samples and control samples. The means for determining the indicator level in a mixed sample determines only the excess of the actual indicator level therein over that in the control sample, and the means for determining the indicator level in a standard sample determined only the excess of the actual indicator level therein over that in the background sample. The analyzer further comprises means for receiving data on the time of injection of the indicator into the blood stream and the time of taking of the mixed samples.

BRIEF DESCRIPTION OF THE DRAWING

The above brief description, as well as further objects and features of the present invention, will be more fully understood by reference to the following detailed description of the presently preferred, albeit illustrative, embodiments of the present invention when taken in conjunction with the accompanying drawing wherein.

DETAILED DESCRIPTION OF THE PREFERRED EMBODIMENTS

Figure 1:
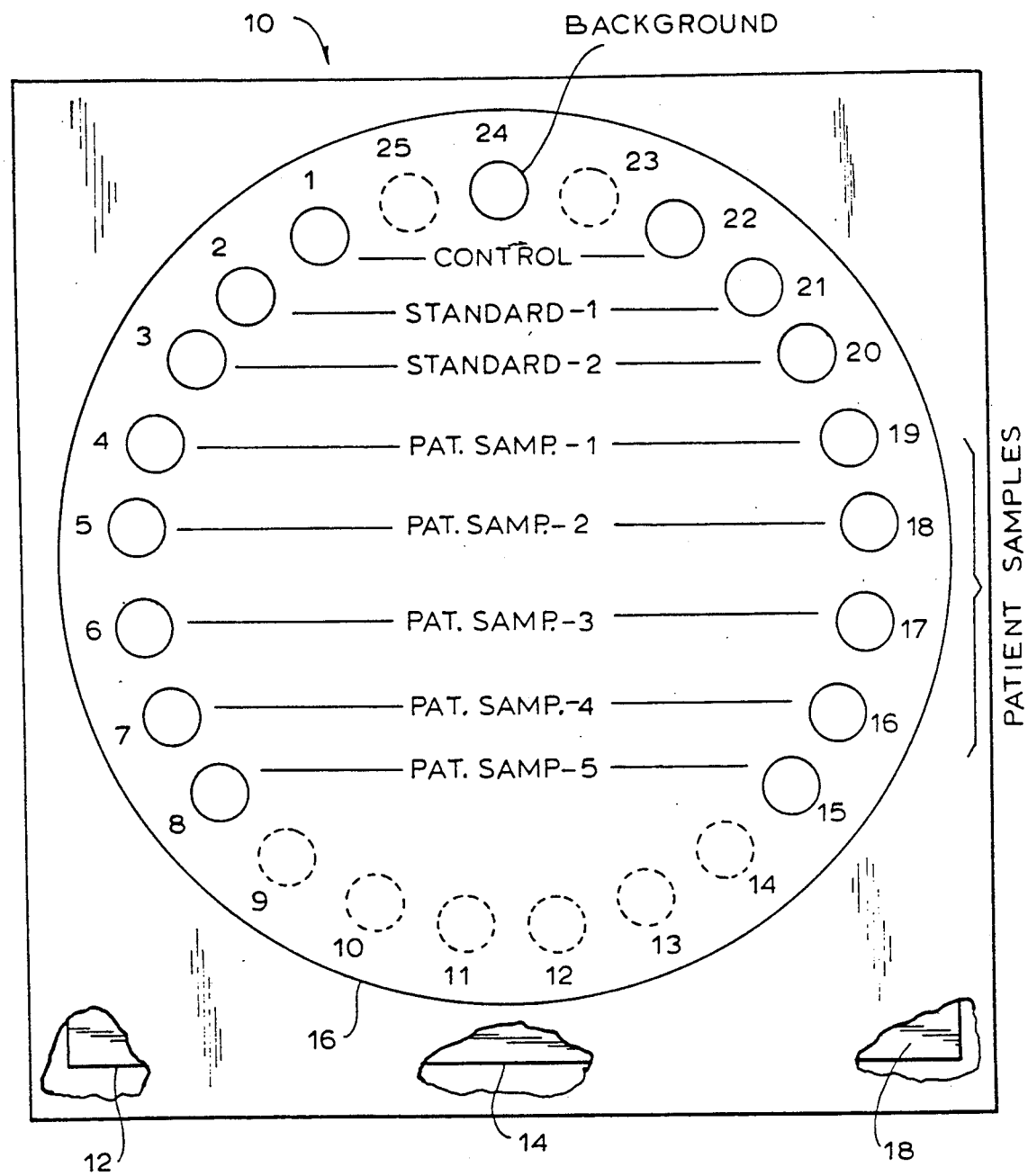
FIG. 1 is a top plan view of an analyzer according to the present invention showing the sample holder, with portions of the analyzer being cut away to reveal details of internal construction.

Referring now to the drawing, and in particular to FIG. 1 thereof, therein illustrated is an automated multipoint time-zero blood volume analyzer, generally designated by the reference numeral 10. The analyzer hardware is of conventional design and consists of a NaI scintillation gamma counter 12, an automatic sample feed mechanism 14 (including a sample holder 16 having spaces for 25 tubes) and a microcomputer 18 running dedicated hardware and software. The microcomputer 18 includes a keyboard or other data entry unit and a CRT, printer or other data display unit.

Overall, the analyzer 10 is a computer-controlled instrument for the direct measurement of human blood volume and associated quantities. The direct measurement is based on the method of tracer dilution utilizing $I^{131}$-tagged serum albumin. The analyzer measures the extent to which the radioactive tracer is diluted when it is dispersed in the patient's bloodstream. The success of the measurement depends on the ability of the circulatory system to distribute the tracer evenly, so that a quantitative measure of dilution can be made. Each sample extracted from the patient after injection with the tracer represents the tracer as diluted into the plasma volume of the patient. The hematocrit is used to convert the plasma volume to whole blood volume.

As the rate of transfer of the tracer across the boundary between the circulatory system and the extra-vascular compartment is proportional to the tracer concentration in each, if one neglects back-leakage (which is negligible over the time-period of the procedure), the concentration of the tracer in the blood decays exponentially. The best estimate of the parameters of a curve which represents several given values of a variable following an exponential curve is achieved by performing a least-squares regression on the log-transformed curve, which is then a straight line. By measuring the concentration of the tracer in blood over time, the desired parameter—the time-zero or equilibrium blood volume—can be estimated.

More particularly, to prepare an injectate manually, a calibrated syringe is filled with $I^{131}$-tagged serum albumin with an activity level ideally between 10 and 20 microcuries. (The isotope is readily available, e.g., from Squibb.) The standards are prepared by injecting 1.00 ml of the tagged albumin into a 1000 ml volumeric flask, diluting to the full 1000 ml volume with sterile saline, mixing, and extracting two 1.00 ml samples. This procedure should then be repeated for the second set of samples. The actual injection is accomplished using the same calibrated syringe, and a separate sterile saline wash solution. Alternately, a pre-calibrated test kit may be made available with the isotope provided as an injectate plus standards. The injectate consists of 1 ml of labelled serum albumin, washed with 20 ml of saline.

The injection should be made into either a running IV line or directly into a vein. To insure adequate mixing of the tracer once it is injected, the vein selected should have flow which can be demonstrated without the use of a tourniquet; a simple test is to lower the IV line below the arm and verify that there is a backflow. The IV line should be flushed with sterile saline after the injection, to insure that the injectate bolus is fully introduced to the bloodstream; a typical volume might be 20-50 ml, depending on the amount of IV tubing used.

Patient blood samples should be collected from a separate, distal IV line at timed intervals. It is important that time is recorded accurately, because the accuracy of the calculation depends directly on the information provided. A control sample should be taken at the time of the isotope injection. The first sample should be taken at about 12 minutes to insure adequate mixing, although in most cases mixing is complete after 8 minutes. The accuracy of the regression is improved if the samples are evenly spaced. The collection of five samples, at 12, 18, 24, 30, and 36 minutes after the initial injection, is recommended. The timing of the intervals is not critical, but accurate recording of the actual sample times is critical.

From each patient blood sample two hematocrit measurements are made, and the results noted for entry into the system. The sample should be centrifuged, and a 1.00 ml portion or specimen of the plasma portion should be placed in each of two 5 ml labelled sample tubes. The specimen tubes should then be sealed and arranged in the numbered holes in the sample changer as shown in the Table. All unspecified positions should be left empty.

TABLE

| Name | Location A | Location B |
| --- | --- | --- |
| Background |  | 24 |
| Control | 1 | 22 |
| Standard-1 | 2 | 21 |
| Standard-2 (if available) | 3 | 20 |
| Pat-Samp-1 | 4 | 19 |
| Pat-Samp-2 | 5 | 18 |
| Pat-Samp-3 | 6 | 17 |
| Pat-Samp-4 (if available) | 7 | 16 |
| Pat-Samp-5 (if available) | 8 | 15 |
| Pat-Samp-6 (if available) | 9 | 14 |

Thus each patient sample is divided into two specimens or aliquots for measuring in tubes 4 and 19, 5 and 18, 6 and 17, 7 and 16, 8 and 15, respectively. In addition to the patient samples taken, there is also a single background sample (measured undivided in tube 24), a control (divided into two specimens for measuring in tubes 1 and 22) and two standards (each divided into two specimens for measuring in tubes 2 and 21 and 3 and 20, respectively). Each of the four standard specimens (for tubes 2-3 and 20-21) represents the same amount of tracer, typically about 15 microcuries, diluted into a given volume of diluent, typically 1000 ml, to provide a reference point for the analyzer. The control sample (for tubes 1 and 22) is taken from the patient before the patient is injected with the tracer, to provide a measurement of the background radioactivity existing in the patient's blood (e.g., from previous blood volume analyses, radiation therapy, etc.). The background sample (for tube 24) consists of a quantity of the diluent used in the standard, without any tracer added thereto, to provide a measurement of the background radioactivity in the environment. Alternatively, tube 24 may be left blank on the assumption that the diluent is non-radioactive. The patient samples (for tubes 4-8 and 14-19), taken after the patient has been injected with the tracer, provide a measurement of the tracer diluted into the plasma volume of the patient.

It is possible, if desired, to assign different specimens to different physical tubes, for the purpose of counting the specimens in a different order. For example, for measuring blood portion volume, in real time as discussed below, the specimens can be arranged in the order in which they become available from the patient.

The count from a patient's sample minus the count of the control represents the count resulting from the introduction of the tracer into the patient's blood stream. The count from the standard minus the count from the background represents the count resulting from the introduction of the tracer into the diluent. From a comparison of the count from a patient s sample (minus the count from the control sample) to the count from the standard (minus the count from the background), the plasma volume can be calculated.

Initially the patient's identification (e.g., name, Social Security number, or both), height, weight and sex are entered on the data entry unit of the microcomputer 18 and thereafter, along with placement of the patient sampler in the sample holder 16, the hematocrit and sample time values are entered. Computer-perceived errors are noted (for example, the times are not in sequence or the hematocrit values exceed a 2% deviation).

To determine a single-point blood volume

The exact formula for the calculation of a single point blood volume G is $$G = 1000*((s-r)/(p-b))*(1/h*.99*.91)$$

where p is the patient count, averaged from two aliquots of the sample, s is the standard count (i.e., from the injectate diluted to 1000 ml), averaged from two aliquots each from two samples, b is the patient background or control, averaged from two aliquots, r is the room background or simply "background", and h is the sample hematocrit, averaged from two measurements (the factor of .99 refers to the plasma packing ratio and .91 refers to the ratio of mean body hematocrit to peripheral (measured) hematocrit).

Figure 2:
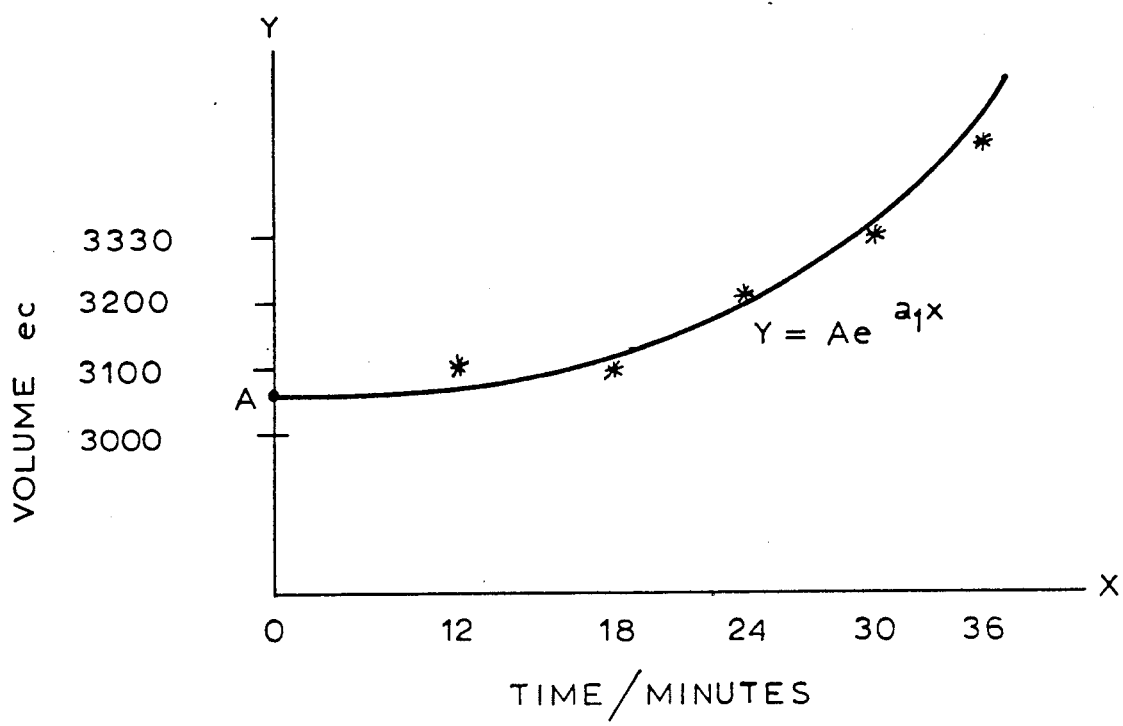
FIG. 2 is a graph of one-point blood volumes Y against elapsed time X.

To determine a time-zero blood volume:

Each patient sample analyzed yields a one-point blood volume. Each blood volume, taken together with the elapsed time information constitutes a set of (X,Y) data points, where X is the elapsed time and Y is the volume. These points represent samples taken along the curve of FIG. 2 defined by:

$$Y = A e^{a_1 x}$$

Where A and $a_1$ are positive constants reflecting the actual status of the patient.

Of particular interest is the value of A, which is the Y-intercept of the curve; i.e., the time-zero volume.

To determine the constants analytically (i.e., to statistically estimate them), a set of data points (X,Y) is derived, where $$Y' = \ln Y = a_o + a_1 X$$

where $a_o = \ln A$.
Then the curve of FIG. 2 approaches the straight line of FIG. 3.

Figure 3:
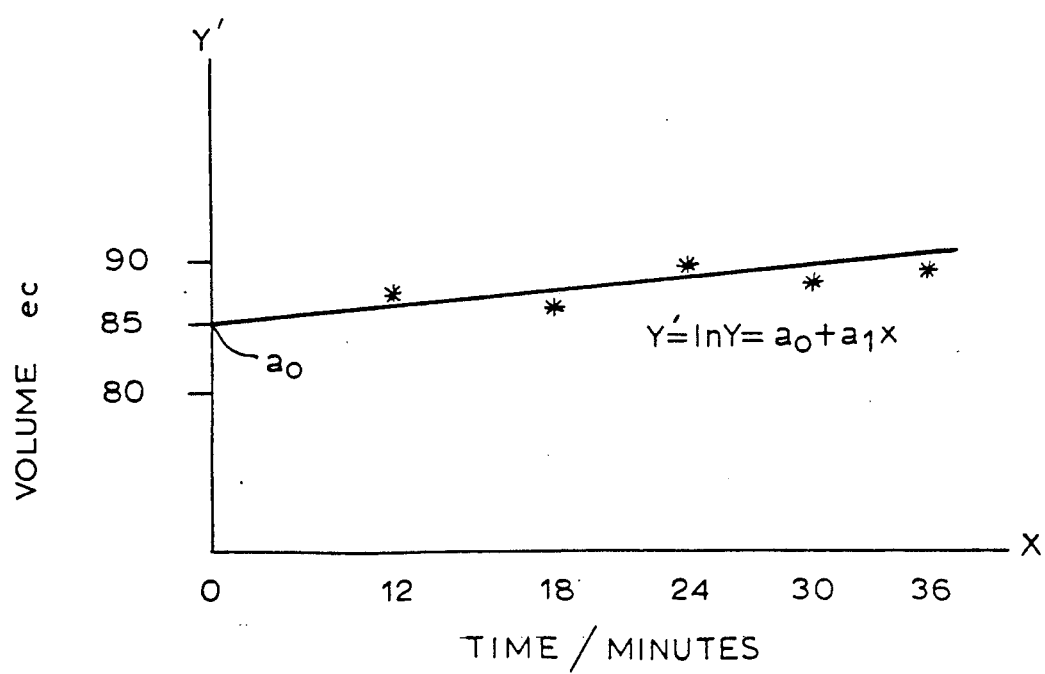
FIG. 3 is a graph of ln Y against elapsed time X.

The standard method for determining the best linear approximation to a set of data points—viz., linear regression by the method of least squares—is applied to the data points of FIG. 3. The line generated is the one in which the sum of the perpendicular distances from each of the data points to the line is minimized. Where m is the number of data points, the formula is:

$$a_o = (S_2 V_o - S_1 V_1) / (S_2 S_o - S_1^2)$$

$$a_1 = (-S_1 V_o + S_o V_1) / (S_2 S_o - S_1^2)$$

where $S_k = \sum_{i=0}^{n} X_i^k$ $(k = 0, 1, 2, \ldots, 2m)$, $V_k = \sum_{i=0}^{n} Y_i X_i$ $(k = 0, 1, 2 \ldots, m)$, and $n = m - 1$ Then $A = e^{a_o}$ is the unadjusted time-zero volume. The number $a_1$ is the slope of the line.

The accuracy of the regression is measured by $$SDa_o = [S2/(S_2 S_o - S_1^2)][S_{min}/(n-1)]$$

$$S_{min} = E[(a_o + a_1 X_i) - Y_i]^2$$

where $SDa_o$ is the standard deviation of the estimate of the constant $a_o$, and
$S_{min}$ is the sum of the distances of the data points to the line.

To determine the ideal blood volume:

Ideal blood volume is calculated based on the height, weight, and sex of the patient. Normal blood volume is not a linear function of either height, weight, or surface area, but rather blood volume per unit weight is a curvilinear function of deviation from ideal weight. For a given height there is an ideal weight for a man and for a woman, based upon values taken from the Metropolitan Life Insurance Company. The patient's deviation from ideal weight is calculated. The ratio of normal blood volume to patient mass is a function of this deviation, with an underweight person having more blood per kilogram of mass than an overweight person. The product of this ratio and the patient's actual weight yields the ideal blood volume for that patient. The range of patient data for which ideal blood volume measurements are available is as follows: ideal weight can be calculated for patients with a height between 53 and 76 inches tall; deviations from ideal weight from −40% to +225% are acceptable.

More particularly, a quantity Q called the (X% desirable wt) is defined by the formula:

$$Q = 100*(\text{actual wt - desirable wt}) / (\text{desirable wt})$$

Q corresponds to a particular blood volume/body mass ratio according to a curvilinear (negative) regression calculated from observed patient data.
Ideal blood volume is then equal to the patient's actual weight times the (blood volume/body mass) ratio Q.

Ideal plasma and red cell volume are calculated from the ideal blood volume and the ideal hematocrit, which is taken to be 45 for men and 39 for women, according to the formula:

Ideal red cell volume = Ideal Hematocrit * .99 * .91 * Ideal blood volume.

The final report from the blood volume analysis contains the figure for the time zero blood volume, and the volumes of the whole blood and plasma components. Deviations from ideal values are also provided. As a general rule of thumb, a ± deviation of less than 8% is considered normal, 8% to 14% is considered mild, 14% to 20% is considered moderate, 20% to 28% is considered severe, and greater than 28% is extreme. Very large deviations should be treated as suspect, subject to verification of the accuracy of the test and the input data (hematocrits, times, and patient height, weight, sex), the counter data, the regression, and the sample collection procedure.

The report also provides a measure of the precision of the regression, reported as the percentage error of the whole blood volume. This figure provides a quantitative measure of how well the points line up.

In order to enable the analyzer to provide useful information in real time, the patient particulars (identification, height, weight, and sex) may be entered and the background and standard specimens analyzed even before the patient is injected with the tracer. Assuming that each specimen requires three minutes of analysis, and that the control is taken and its analysis begun concurrently with the injection of the injectate into the patient, eight patient specimens should be analyzable before the last patient sample is taken (about 36 minutes after the initial injection using the recommended 12, 18, 24, 30, 36 spacing of patient sample taking). Analysis of the remaining two specimens (assuming five patient samples are used) would require about another six minutes. Assuming that the pertinent hematocrit and time interval data were timely entered, the final results should be available within an additional five seconds. Thus final results are available in real time—i.e., within a reasonable period of time (about six minutes) after the last patient sample has been taken. Generally at least three patient samples are recommended.

If a sampling error is made, then one point of the regression will be significantly out of line with the others. The system checks for this, and will print an alternate set of figures if it determines that it is likely that this has occurred. If it is apparent that one of a pair of counts (either a sample or standard) is out of line, and which one of the pair is apparent by comparison with the other counts, then the erroneous count can be edited to be the same as the other count of the pair.

Clearly the principles of the present invention are equally applicable for use with tracers other than the recommended $I^{131}$-tagged serum albumin. For example, other radioactive isotopes of iodine may be used to tag the serum albumin, other tagged proteins may be utilized, etc.

To summarize, the method of the present invention enables the measurement of blood volume to be obtained by direct measurement techniques using a true time-zero blood volume from a multi-point calculation. The method optionally compares the calculated blood volumes to an ideal blood volume for the patient. The present invention further provides an analyzer for carrying out the method in real time.

Now that the preferred embodiments of the present invention have been shown and described in detail, various modifications and improvements thereon will become readily apparent to those skilled in the art. Accordingly, the appended claims are to be construed broadly in a manner consistent with the spirit and scope of the present invention.

I claim:
1. A multi-point method of determining a time-zero blood volume by the indicator dilution technique comprising the steps of:
   (A) injecting an indicator into the blood stream of a living being;
   (B) removing a plurality of mixed samples of blood and indicator from the blood stream at a corresponding plurality of measured time intervals subsequent to the injecting step and determining the hematocrit of each mixed sample;
   (C) providing means for automatically determining the level of indicator in a plasma portion of each of the mixed samples relative to prepared standards, for automatically calculating for each mixed sample the apparent plasma volume from the indicator level, for automatically calculating for each mixed sample the apparent blood volume from the apparent plasma volume and hematocrit, for automatically calculating a time-zero blood volume from the calculated apparent blood volumes and time intervals, and for recalculating the time-zero blood volume without using any calculated apparent blood volume which reflects an indicator level which is out of line with the others; and
   (D) providing as input to such means plasma portions of the mixed samples, the hematocrits, and the time intervals and causing said means to automatically calculate the time-zero blood volume.

2. The method of claim 1 wherein in step (D) the time-zero blood volume is calculated by logarithmic regression analysis.

3. The method of claim 1 wherein prior to step (D) the blood volume/time interval data is analyzed for general agreement, and any such data not in general agreement with the remainder of such data is disregarded in the determination of the time-zero blood volume.

4. The method of claim 1 wherein the indicator is a radioactive tracer and in step (C) the determination of the indicator level employs a gamma counter.

5. The method of claim 4 wherein the tracer is $I^{131}$-tagged serum albumin and the gamma counter is an NaI scintillation gamma counter.

6. The method of claim 1 wherein in step (B) the time intervals are irregular.

7. The method of claim 1 wherein said determination of a time-zero blood volume is made in real time.

8. An automated real-time multi-point, time-zero blood volume analyzer comprising:
   (A) means for receiving a plasma portion of each of a plurality of mixed samples of blood and an indicator injected into a blood stream from which the sample is taken, the indicator having been injected at a given time and the samples being taken at measured time intervals thereafter;
   (B) means for receiving data one the time of injection of the indicator into the blood stream, the time of taking each of the mixed samples, and the hematocrit of each of the mixed samples;
   (C) means for automatically determining the level of indicator in the plasma portion of each of the mixed samples relative to prepared standards, for automatically calculating for each mixed sample the apparent plasma volume from the indicator level, for antomatically calculating for each mixed sample the apparent blood volume from the apparent plasma volume and hematocrit, for automatically calculating a time-zero blood volume from the calculated apparent blood volumes and time intervals, and for recalculating the time-zero blood volume without using any calculated apparent blood volume which reflects an indicator level which is out of line with the others.

9. The analyzer of claim 8 further comprising means for receiving an environment background sample, a standard sample, and a control sample, and means for determining as the indicator level in a mixed sample only the excess of the actual indicator level therein over that in the control sample, and means for determining as the indicator level in a standard sample only the excess of the actual indicator level therein over that in the background sample.

10. The analyzer of claim 8 further comprising means for receiving an environment background sample and a standard sample, and means for determining as the indicator level in a standard sample only the excess of the actual indicator level therein over that in the background sample.

11. The analyzer of claim 10 wherein said means for determining the indicator level in a mixed sample determines the same by reference to determined indicator levels in a standard sample.

12. The analyzer of claim 8 further comprising means for receiving data representing the patient's sex, height and weight and for calculating and displaying the ideal blood volume for the patient.

* * * * *